United States Patent
Ibrahim et al.

(10) Patent No.: US 10,597,506 B2
(45) Date of Patent: Mar. 24, 2020

(54) PROCESS FOR EXTRACTION OF BIOPLASTIC AND PRODUCTION OF MONOMERS FROM THE BIOPLASTIC

(71) Applicant: BIOEXTRAX AB, Malmö (SE)

(72) Inventors: Mohammad H.A. Ibrahim, Lund (SE); Mohamad Takwa, Malmö (SE); Rajni Hatti-Kaul, Lund (SE)

(73) Assignee: BIOEXTRAX AB, Malmo (SE)

( * ) Notice: Subject to any disclaimer, the term of this patent is extended or adjusted under 35 U.S.C. 154(b) by 0 days.

(21) Appl. No.: 15/529,028

(22) PCT Filed: Nov. 25, 2015

(86) PCT No.: PCT/SE2015/051268
§ 371 (c)(1),
(2) Date: May 23, 2017

(87) PCT Pub. No.: WO2016/085396
PCT Pub. Date: Jun. 2, 2016

(65) Prior Publication Data
US 2017/0253713 A1   Sep. 7, 2017

(30) Foreign Application Priority Data
Nov. 25, 2014 (SE) .................. 1451422-8

(51) Int. Cl.
| | |
|---|---|
| *C12P 7/40* | (2006.01) |
| *C12P 7/42* | (2006.01) |
| *C12N 1/20* | (2006.01) |
| *C12N 9/88* | (2006.01) |
| *C08J 11/10* | (2006.01) |
| *C12P 7/62* | (2006.01) |
| *C12N 1/06* | (2006.01) |
| *C12R 1/07* | (2006.01) |
| *C08L 101/16* | (2006.01) |

(52) U.S. Cl.
CPC ........... *C08J 11/105* (2013.01); *C08L 101/16* (2013.01); *C12N 1/06* (2013.01); *C12N 1/20* (2013.01); *C12P 7/42* (2013.01); *C12P 7/625* (2013.01); *C12R 1/07* (2013.01); *C08J 2367/04* (2013.01)

(58) Field of Classification Search
CPC .... C12N 9/88; C12N 1/20; C12N 1/06; C12P 7/18; C12P 7/42; C12P 7/62; C12R 1/07
USPC ....................... 435/135, 252.3, 41
See application file for complete search history.

(56) References Cited

FOREIGN PATENT DOCUMENTS

| | | |
|---|---|---|
| WO | WO 2006103699 A1 | 10/2006 |
| WO | WO 2008065749 A1 | 6/2008 |
| WO | WO 2011112154 A1 | 9/2011 |
| WO | WO 2011145683 A1 | 11/2011 |
| WO | WO 2012149162 A2 | 11/2012 |
| WO | WO 2014032633 A1 | 3/2014 |
| WO | WO 2014079844 A1 | 5/2014 |

OTHER PUBLICATIONS

Hui et al.( PNAS 2007, 104, pp. 5722-5726.*
Elbanna K et al., "*Schlegelella thermodepolymerans* gen. nov.,sp. nov., a novel thermophilic bacterium that degrades poly(3-hyd roxybutyrate-co-3-mercaptopropionate )", International Journal of Systematic and Evolutionary Microbiology, 2003, vol. 53, pp. 1165-1168.
Elbanna K et al., "Studies on the biodegradability of polythioester copolymers and homopolymers by polyhydroxyalkanoate (PHA)-degrading bacteria and PHA depolymerases", 2004, Arch Microbial, val. 182, pp. 212-225.
El-Refai H. A. et al., "Improvement of the newly isolated 1-4 Bacillus pumilus FH9 keratinolytic activity", Process Biochemistry, 2005, vol. 40, pp. 2325-2332.
Lakshman K et al., "Extraction of polyhydroxyalkanoate from Sinorhizobium meliloti cells using Microbispora sp culture and its enzyme", 2006, val. 39, pp. 1471-1475; the abstract; p. 1473, table 1 and p. 3.2.
Wemhoff S et al., "Generation of biologically contained, readily transformable, and genetically manageable mutants of the biotechnologically importants Bacillus pumilus", Appl Microbial Biotechnol, 2013, vol. 97, pp. 7805-781 9.
Brack C et al., "2,5-Diketopiperazines produced by Bacillus pumilus during bacteriolysis of Arthrobacter citreus", Mar Biotechnol, 2014, val. 16, pp. 385-395; the abstract; p. 394, left column, paragraph 4.
International Search Report dated Feb. 23, 2016 for PCT Application No. PCT/SE2015/051268.

* cited by examiner

*Primary Examiner* — Robert B Mondesi
*Assistant Examiner* — Mohammad Y Meah
(74) *Attorney, Agent, or Firm* — Moser Taboada

(57) ABSTRACT

The present invention relates to a process for extraction of bioplastic from bioplastic-producing microbial cells, comprising the steps of: A. providing bioplastic producing microbial cells comprising bioplastic; B. providing bacterial cells selected from the species *Bacillus pumilus*; C. extracting the bioplastic by admixing the bioplastic-producing microbial cells of step A and the bacterial cells of step B and allowing reaction. The present invention further relates to the process of producing monomers from said bioplastics by depolymerization.

15 Claims, 10 Drawing Sheets

Figure 1:
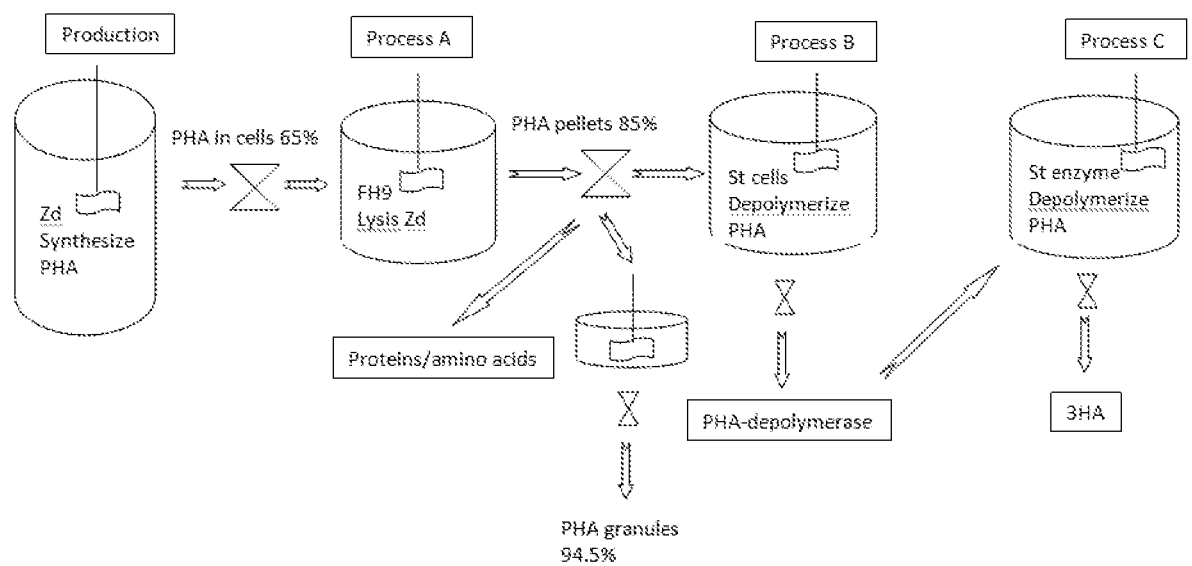

PROCESS FOR EXTRACTION OF BIOPLASTIC AND PRODUCTION OF MONOMERS FROM THE BIOPLASTIC

FIELD OF THE INVENTION

The present invention relates to a bio-based process for extraction and depolymerization of bioplastics from bioplastic-producing microbial cells.

TECHNICAL BACKGROUND

After the oil crisis and during the past three decades, biopolymers produced from biomass and having properties suitable for use as plastics, hence called as bioplastics, have gained a lot of interest as renewable alternative to petroleum based plastics. Among the several different types of bioplastics are polyhydroxyalkanoates (PHAs) that belong to the polyester class of polymers. Many bacterial and archaeal strains can accumulate PHA granules as intracellular carbon and energy reserves.

Poly(3-hydroxybutyrate), (PHB), is a homopolymer and is the most common type of PHA produced by microorganisms. Several microbial strains are also able to produce other PHA homopolymers or copolymers with varying monomer composition such as poly(hydroxybutyrate-co-hydroxyvalerate) (PHBV), poly(hydroxybutyrate-co-hydroxyhexanoate) (PHBHx), poly(hydroxyoctanoate-co-hydroxyhexanoate) (PHOHx), etc.

PHAs are of interest as bio-derived and biodegradable plastics and have properties similar to the widely used fossil based plastics, polyethylene and polypropylene. Examples of properties may be thermoplasticity, good resistance to moisture, aroma barrier properties, etc. Also, the possibility to produce PHAs with different properties by varying the monomer composition, using different renewable carbon sources, and their complete biodegradability upon being decomposed in soil, make PHAs highly interesting substitutes for conventional plastics. Moreover, PHAs show great biocompatibility in different pharmaceutical and medicinal applications, in addition to their promising industrial and agricultural applications.

Polylactic acid or polylactide (PLA) is also a biodegradable aliphatic bioplastic derived from renewable resources, such as corn starch, tapioca roots, chips or starch, or sugarcane. PLA, like PHA, belong to the polyester class. Synthesis of PLA by recombinant bacteria has also been reported.

In WO14032633 a method for producing polyhydroxyalkanoates from oil substrate is disclosed. Further, in WO12149162 production of polyhydroxyalkanoate with genetically engineered microbes is disclosed.

There are however several drawbacks to the processes and methods known today, and e.g. described in these documents. Processes for production of PHA bioplastics involve methods of extracting the produced bioplastic material from the microbial cells producing said bioplastic. Today such methods involve various chemicals as part of the process. Chemicals that could be used to extract the bioplastic from the cells may be chosen from organic solvents, detergents, acid, alkali, or hypochlorite. The use of different types of chemicals in the production of bioplastics is both costly and not desirable due to their high environmental impact.

Attempts have been made to circumvent these drawbacks. WO08065749 and WO11145683 disclose methods for producing natural polymeric substances for molding of a biodegradable material. In the documents the method of extraction utilizes a time consuming drying and grinding step providing an end product of low purity.

There is a need to provide bioplastics in more environment-friendly and cost efficient ways in order to be competitive with the petrochemically derived plastics.

On the other hand, PHAs are regarded to be a novel renewable source for enatiomerically pure chemicals via depolymerization of PHAs into its monomeric composition, R-3-hydroxyalkanoic acids (R-3-HAs). Because of the interesting industrial and medical applications of R-3-HAs, different chemical and biological depolymerization methods are being investigated to achieve an economic and easy-to-apply process for R-3HA production from PHA.

SUMMARY OF THE INVENTION

According to one aspect of the present invention there is provided a process for extraction of bioplastic from bioplastic-producing microbial cells, comprising the steps of:
A. providing bioplastic producing microbial cells comprising bioplastic;
B. providing bacterial cells selected from the species *Bacillus pumilus;*
C. extracting the bioplastic by admixing the bioplastic-producing microbial cells of step A and the bacterial cells of step B and allowing reaction.

In one embodiment the bacterial cells are of the genus *Bacillus*. In one embodiment the bacterial cells are of the species *Bacillus pumilus*. In one embodiment the bacterial cells are of *Bacillus pumilus* FH9. In one embodiment the extraction includes a lysis step. In one embodiment the extraction comprises a lysing bacterial cell. In one embodiment, said lysing bacterial cell is preferably originated from the strain FH9 or its extracellular enzymes. In one embodiment the bacterial cells are selected from the group comprising biomass-degrading-enzymes producing bacteria.

In another embodiment the extraction process further is comprising a separation step, wherein proteins, peptides, or amino acids or any combinations thereof are separated from the bioplastic. In another more specific embodiment the separation is performed by decantation, filtration, centrifugation, aggregation, air flotation or precipitation or any combinations thereof. One embodiment is further comprising a washing step preferably after extraction and separation to wash the obtained bioplastic. In one embodiment, said washing step is preferably performed using water as washing liquid.

In one embodiment, said bioplastic-producing microbial cells are bacterial cells. In one embodiment said bioplastic-producing microbial cells are bacterial or archaeal strains. In one embodiment said bioplastic-producing microbial cells are selected from a strain selected from the group *Ralstonia, Halomonas, Zobellella, Pseudomonas, Alcaligenes, Bacillus, Chromobacterium*, recombinant *Eschericha coli* or any combinations thereof. Other PHA-accumulating strains or other bioplastic-producing microbial cells or mixed cultures could be used.

In one embodiment the bioplastic is a polyester. In one embodiment said bioplastic is a linear polyester. In another embodiment the bioplastic is selected from different polyhydroxyalkanoates (PHAs), such as poly(3-hydroxypropionate) (PHP or P3HP), poly(3-hydroxybutyrate) (PHB or P3HB), poly(4-hydroxybutyrate) (P4HB), poly(3-hydroxyvalerate) (PHV or P3HV), poly(4-hydroxyvalerate) (P4HV), poly(5-hydroxyvalerate) (P5HV), poly(3-hydroxyhexanoate) (PHHx or P3HHx), poly(3-hydroxyoctanoate) (PHO, or P3HO), poly(3-hydroxydecanoate) (PHD or P3HD), poly(3- hydroxyundecanoate) (PHU, P3HU), or other short- or medium-chain length, saturated or unsaturated PHAs; or polylactic acid (PLA); or their copolymers or any combinations thereof.

In one embodiment of the present invention no organic solvent or chemicals or any combinations thereof are used in the extraction process.

One aspect of the present invention is a process of producing monomers from bioplastic, comprising:
- D. providing extracted bioplastic produced using the process for extraction according to the present invention,
- E. providing a depolymerization substance; and
- F. depolymerising the bioplastic polymer by admixing the bioplastic of step D and the depolymerization substance of step E and allow reaction.

In one embodiment, the provision of the depolymerization substance is provided via addition of microbial cells producing said bioplastic depolymerization substance. In one embodiment, said added microbial cells produce a thermostable extracellular PHA depolymerase. In one embodiment said microbial cells are selected from the strain *Schlegelella thermodepolymerans* K14. In another embodiment the process of the present invention is further comprising a separation step for retrieval of the depolymerization substance. In one embodiment, said process further comprises the steps of:
- G. providing bioplastic produced according to the process for extraction of bioplastic from bioplastic producing microbial cells mentioned above;
- H. providing the depolymerization substance from steps E and/or F to the bioplastic;
- I. admixing bioplastic of step G and depolymerization substance of step H and allow reaction, to obtain monomers of the bioplastic, with the proviso that the provision of the depolymerising substance of step H is performed by addition of microbial cells which produce the depolymerization substance in step E and/or F. In another embodiment, the provision of the depolymerization substance is provided via addition of microbial cells producing said bioplastic depolymerization substance. In one embodiment said produced bioplastic depolymerization substance is a thermostable extracellular PHA depolymerase. In one embodiment said microbial cells are selected from the strains *Schlegelella thermodepolymerans* K14 or PHA depolymerizing microorganism.

In one embodiment of the present invention, the bioplastic is a linear polyester. In one embodiment said bioplastic is polyhydroxyalkanoate (PHA).

Another aspect of the present invention is a biopolymer composition obtainable by the process according to the present invention comprising a purity of biopolymer of at least 88%, preferably at least 90%, preferably at least 95%, preferably at least 97%, preferably at least 98%.

Yet another aspect of the present invention relates to the use of a bioplastic extracted according to the present invention for the production of products selected from the group comprising bioactive nanobeads, biocompatible products, biodegradable or renewable products, thermoplast, elastomer products or polymer precursors. In one embodiment the present invention relates to the use of products chosen from the group comprising coatings, foils, diapers, wastebags, tyres, packaging, single use articles, protein purification matrix, implant parts, bone replacements, slow release drug or fertilizer/pesticide carriers.

One embodiment relates to the use of a bioplastic extracting process for the production of monomers. In one embodiment, said monomers are preferably hydroxyalkanoate (HA) monomers.

Another embodiment relates to the use of a bioplastic extracting process for the production of proteins, peptides, or amino acids or any combinations thereof. One embodiment relates to the use of the bioplastic extracting process for production of waste proteinaceous biomass preferably from the microbial fermentation industry or agro or animal/poultry industries. Yet another embodiment relates to the use of a bioplastic extraction process for the production of biopolymers with a purity of 95% comprising no use of a organic solvents.

In one embodiment the present invention relates to use of a bioplastic extracting process according to the present invention for the production of monomers from linear polyesters. Another embodiment relates to use of a bioplastic extracting process according to the present invention for production of a bioplastic or monomers thereof are selected from the group polyhydroxyalkanoates (PHAs): poly(3-hydroxypropionate) (PHP or P3HP), poly(3-hydroxybutyrate) (PHB or P3HB), poly(4-hydroxybutyrate) (P4HB), poly(3-hydroxyvalerate) (PHV or P3HV), poly(4-hydroxyvalerate) (P4HV), poly(5-hydroxyvalerate) (PSHV), poly(3-hydroxyhexanoate) (PHHx or P3HHx), poly(3-hydroxyoctanoate) (PHO, or P3HO), poly(3-hydroxydecanoate) (PHD or P3HD), poly(3-hydroxyundecanoate) (PHU, P3HU), or other short- or medium-chain length, saturated or unsaturated PHAs; or polylactic acid (PLA); or their copolymers or any combinations thereof.

In another specific embodiment the present invention relates to use of a bioplastic extracting process for the production of microbial intracellular polymers. In one embodiment said microbial intracellular polymers are selected from the group lipids (preferably triacylglycerol or TAGs), polyanhydride particles (preferably polyphosphate) or polysaccarides (preferably glycogen).

In one embodiment the present invention relates to the use of bacterial strain according to the present invention, for lysing bioplastic producing bacterial cells.

SHORT DESCRIPTION OF THE DRAWINGS

FIG. 1. shows a generalized flowchart of the Invention. Bio-based process for extraction of PHA from microbial cells (A), bacterial depolymerization of recovered PHA granules (B), enzyme depolymerization of recovered PHA granules into its monomers (C).

Figure 2:
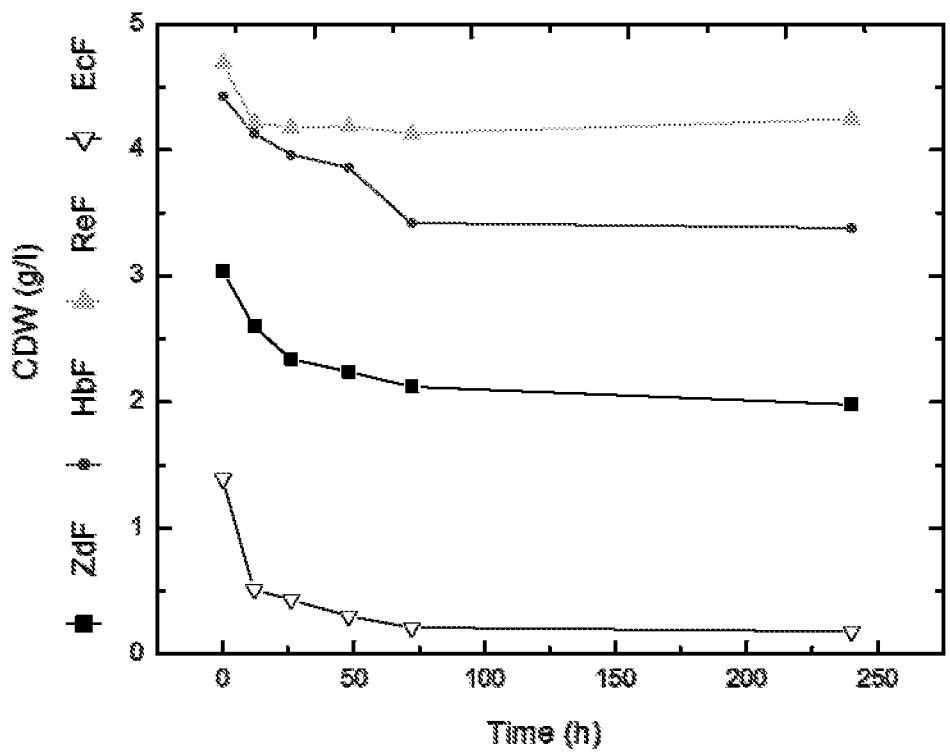
Figure 2:
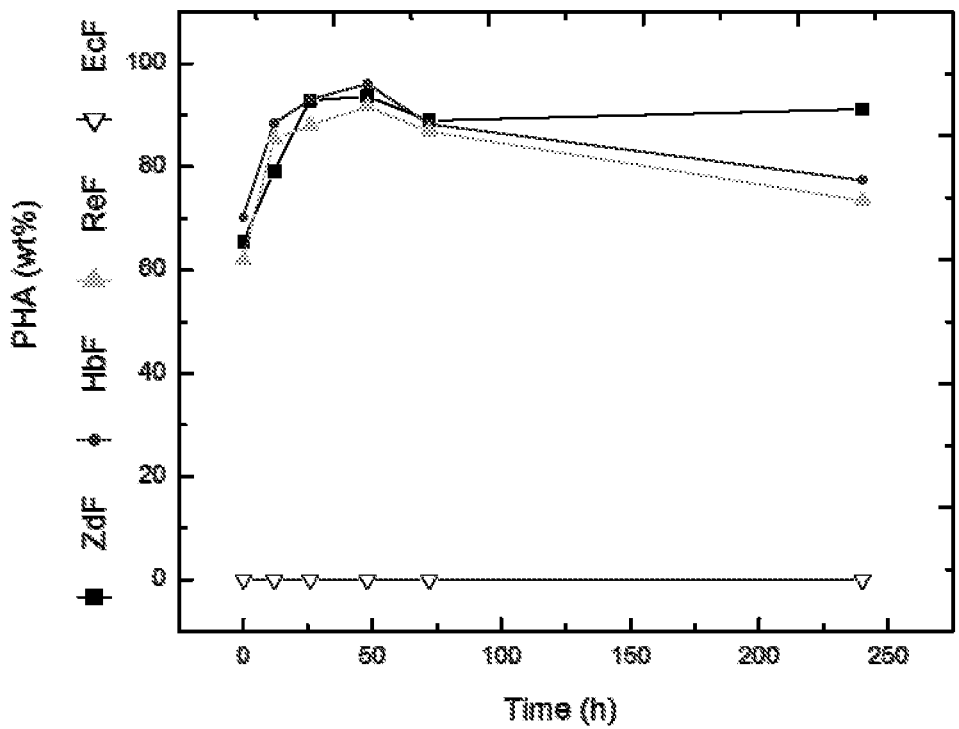

FIG. 2. shows extraction of PHA via lysis of non-PHA cellular materials of different PHA-accumulating bacterial stains, *Z. denitrificans* (ZdF); *H. boliviensis* (HbF); *R. eutropha* (ReF); recombinant *E. coli* (EcF). Effect of inoculation of lytic strain FH9 on CDW of the recovered pellets (A), Effect of inoculation of lytic strain FH9 on PHA content of the recovered pellets (B). Time course of cell dry weight and PHA content were analyzed at different time intervals upon inoculation of the lytic cells FH9 in basal medium supplemented with different PHA accumulating strains separately in 1-litter flasks along 10 days (240 h).

Figure 3:
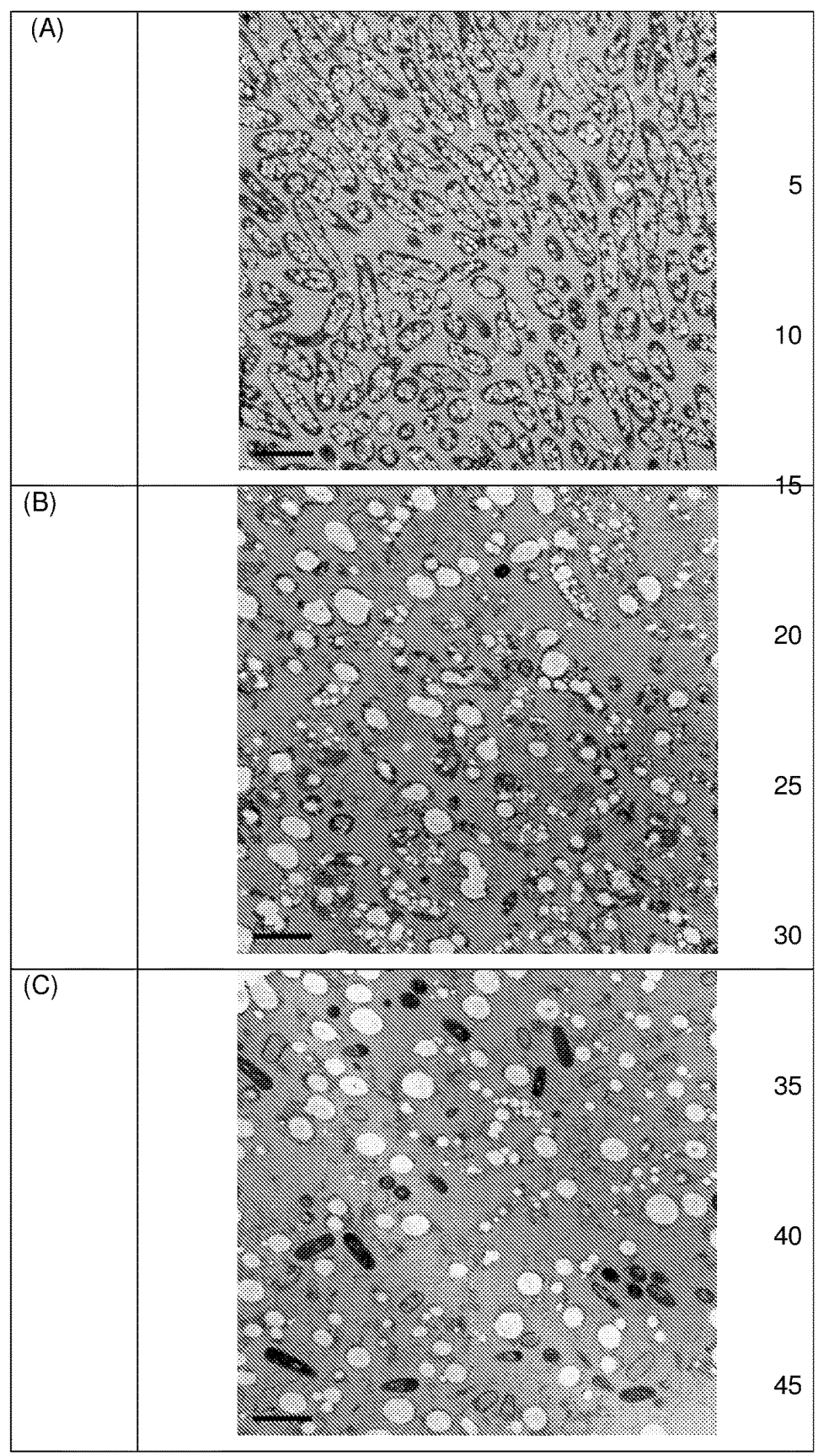

FIG. 3. shows electron microscope photographs of bioplastic-producing microbial cells at different time intervals of lysis: 0, 6, and 24 hours. The black bar at the bottom left corner equals 2 μm.

Figure 4:
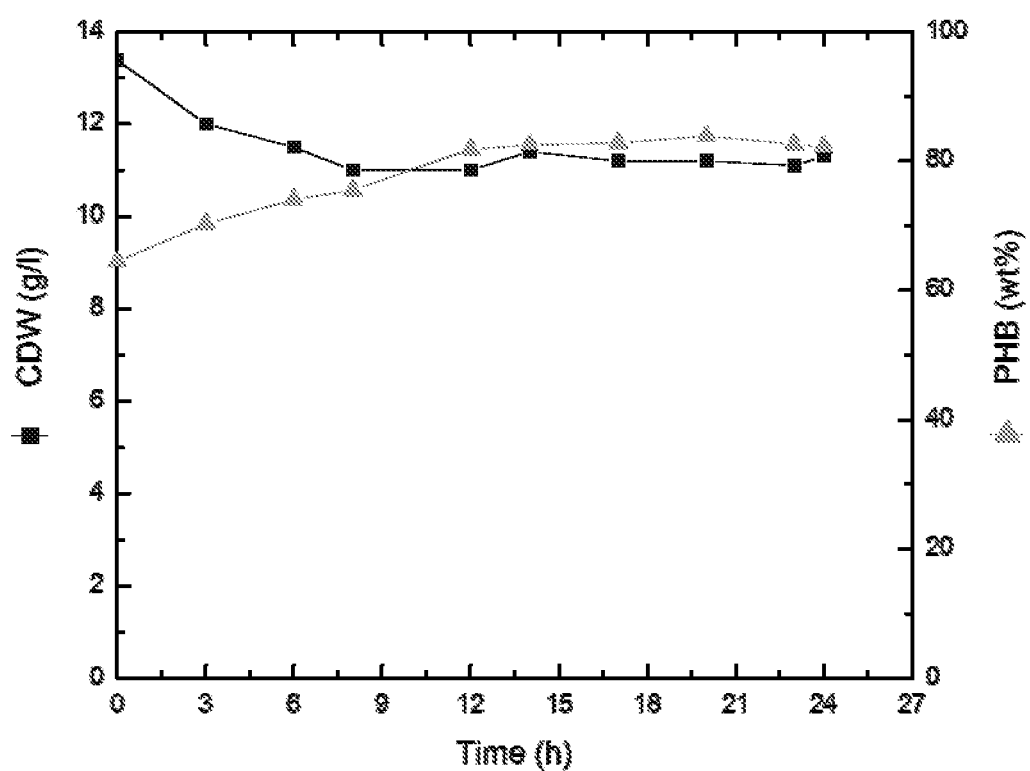

FIG. 4. shows a graph illustrating the PHB content of unwashed pellets recovered from a process of extraction of PHB. The X-axis represents lysis time in hours, and the Y-axes represent the cell dry weight of recovered pellets and percent of recovered PHB (with respect to CDW, wt %).

Figure 5:
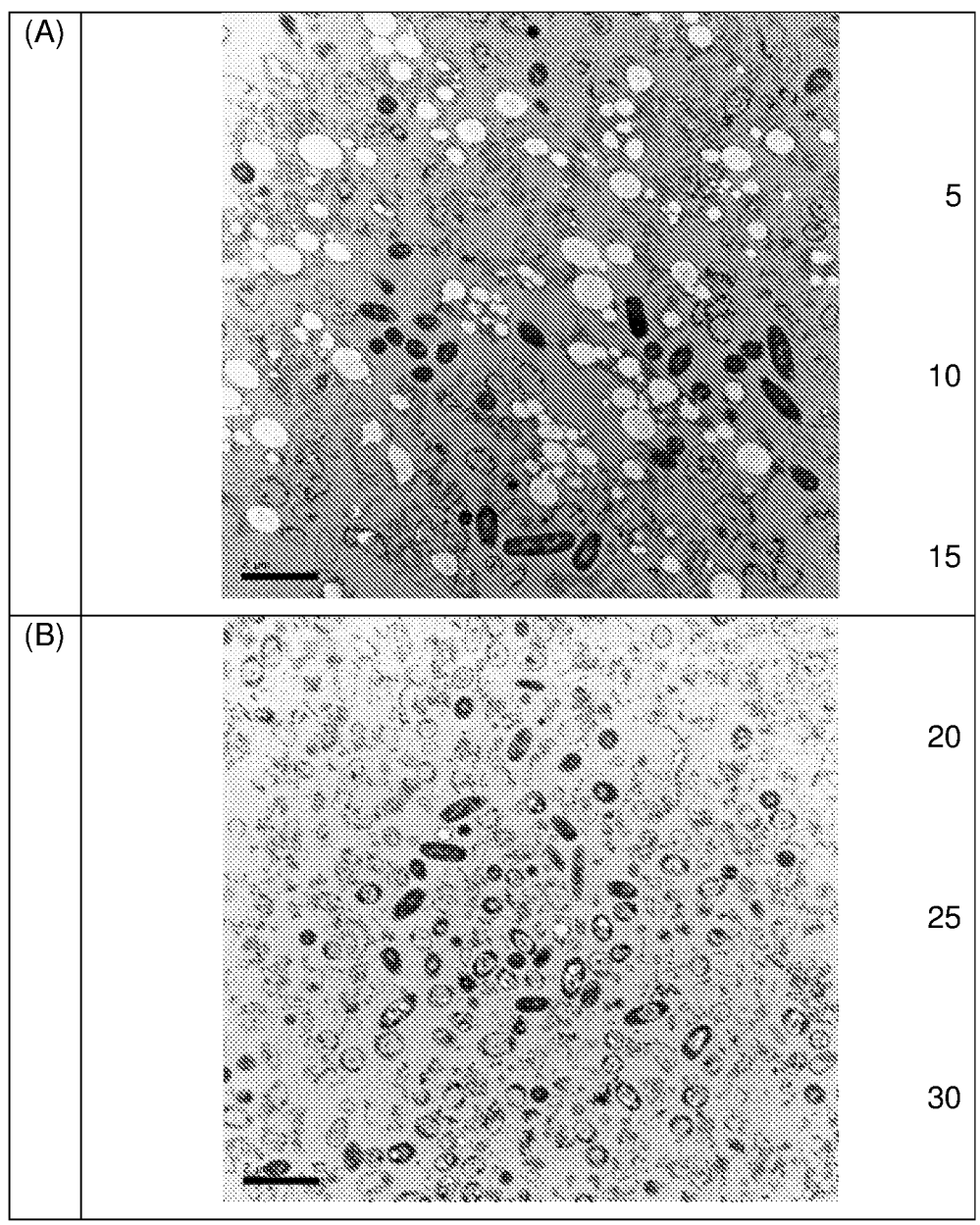

FIG. 5. shows electron micrographs of reactants before and after depolymerization (0 h and 39 h) illustrating the degradation of the bioplastic granules. Note, that the PHA-depolymerizing cells, while being able to degrade all released PHA granules, could not attack PHA granules which were still inside some intact cells (cells that had failed to be lysed in a previous step).

Figure 6:
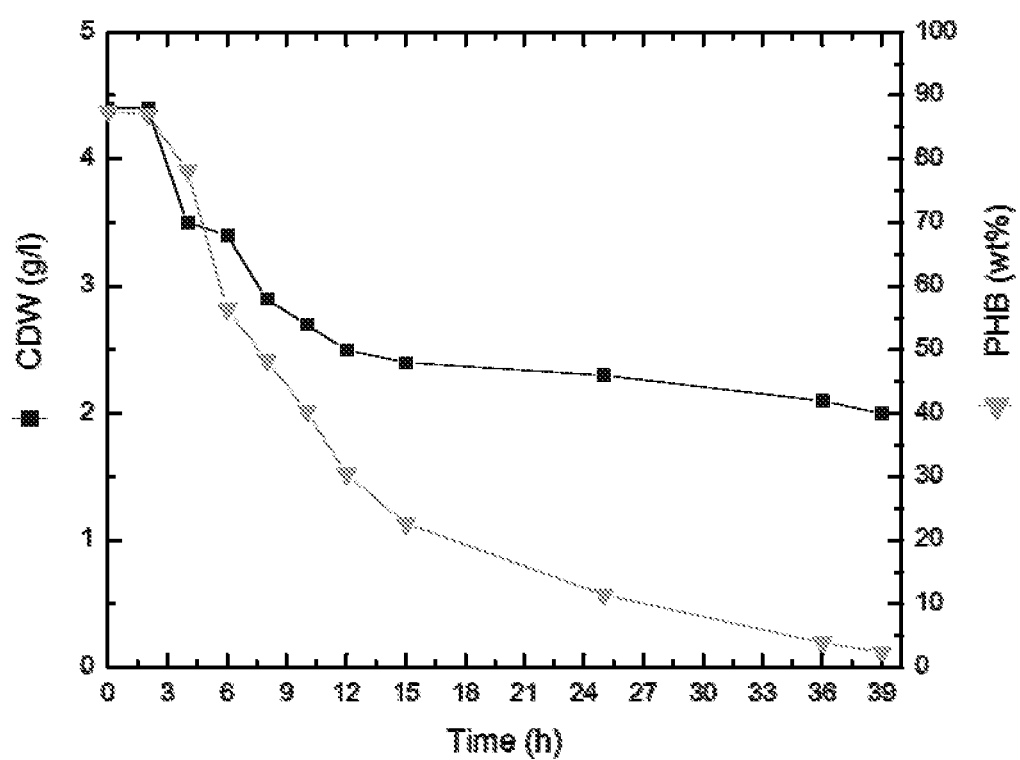

FIG. 6. shows a graph illustrating the PHB content (wt %) recovered from the lysis process according to one aspect of the present invention i.e. extraction of bioplastic through lysis of the microbial cells and then depolymerization of the bioplastic granules.

Figure 7:
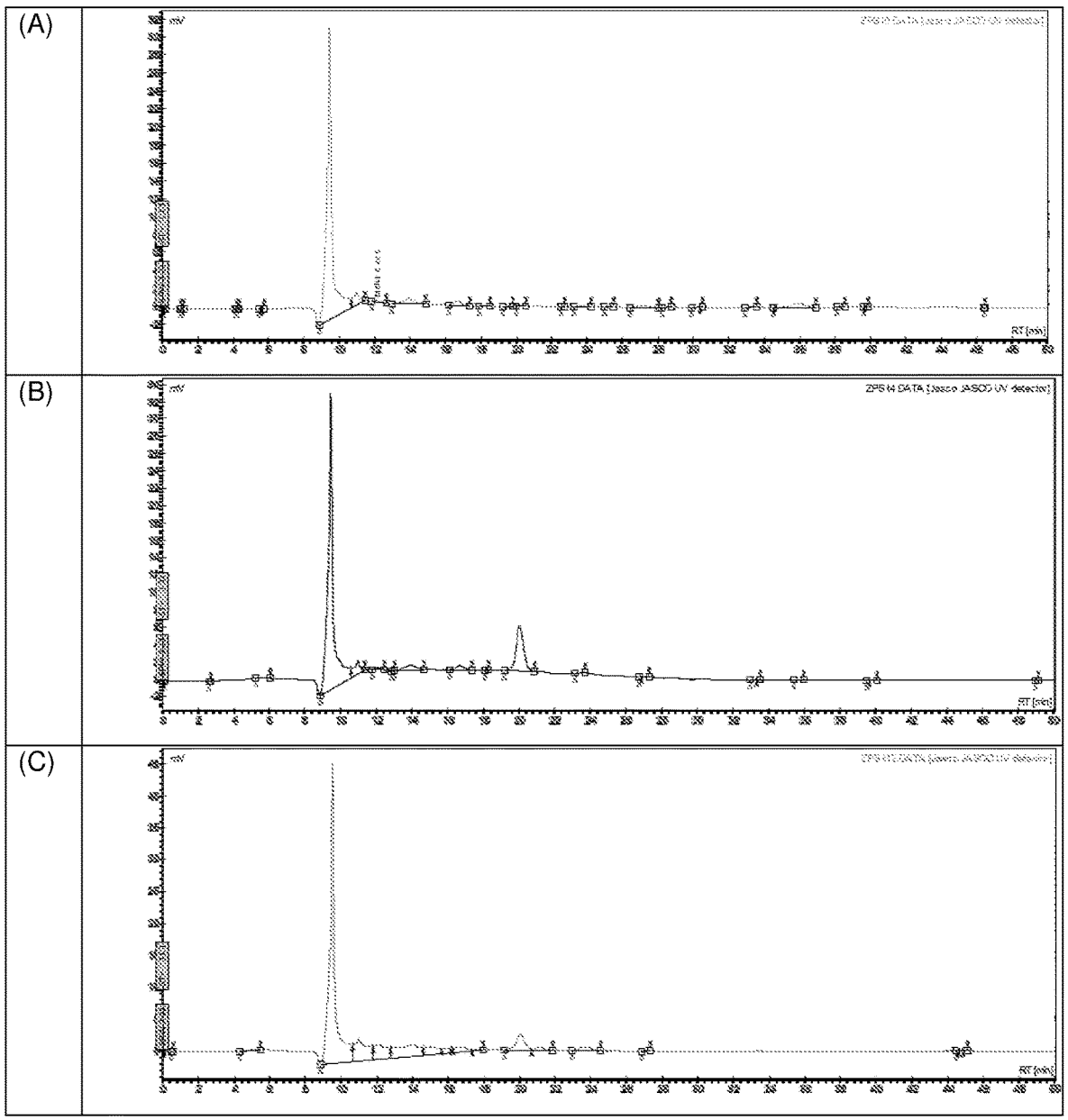

FIG. 7. shows chromatograms illustrating how a peak at about 20 minutes, symbolizing the amount of PHB monomers (3HB), which increases with time, then decreases once the PHA-depolymerizing cells start consuming the depolymerization products.

Figure 8:
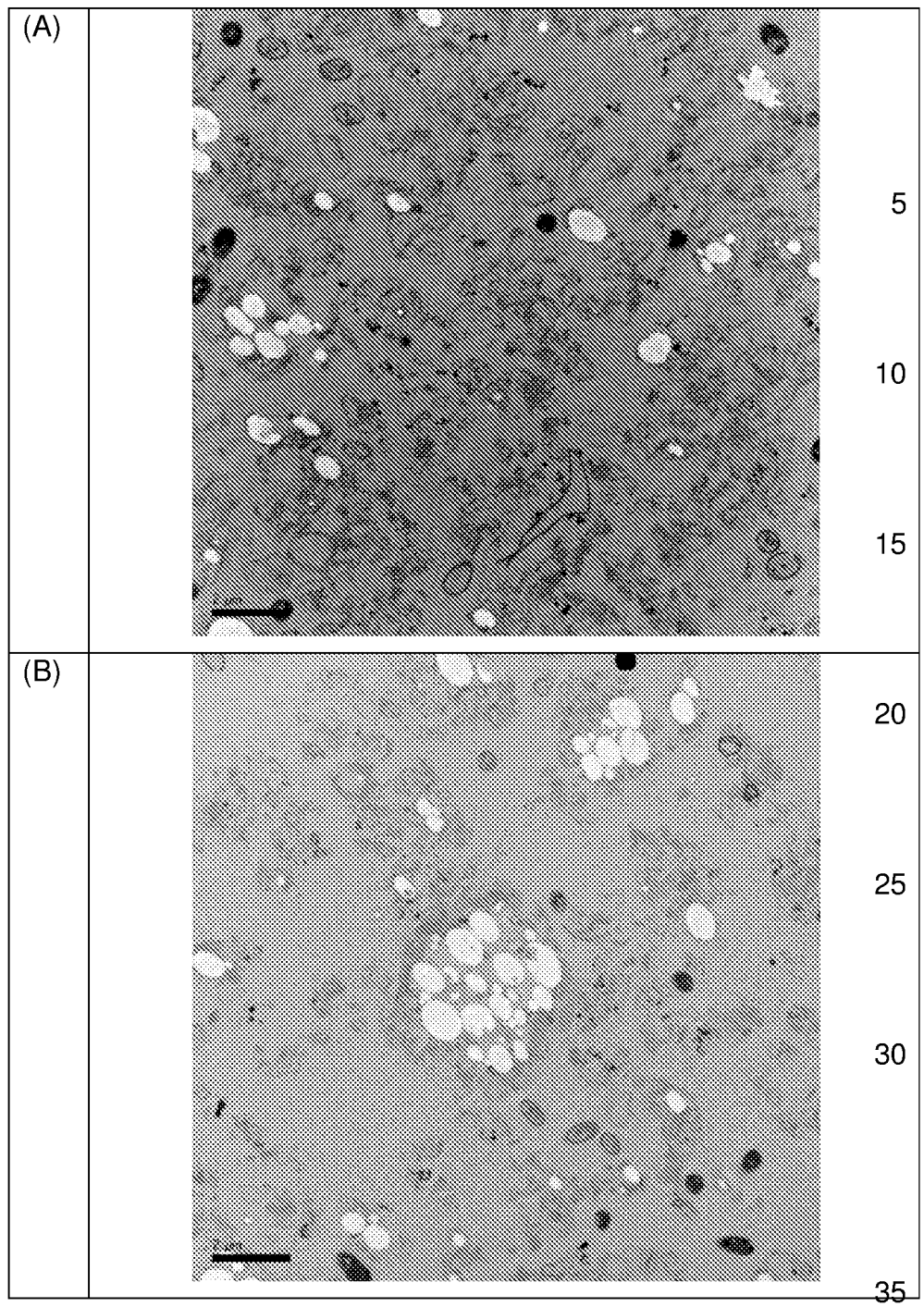

FIG. 8. shows an electron micrograph of PHA granules at different times of enzyme depolymerization (2 h and 8 h), illustrating the effect of PHA-depolymerase on sides of some granules as a direct physical contact to facilitate the bioplastic depolymerization process.

Figure 9:
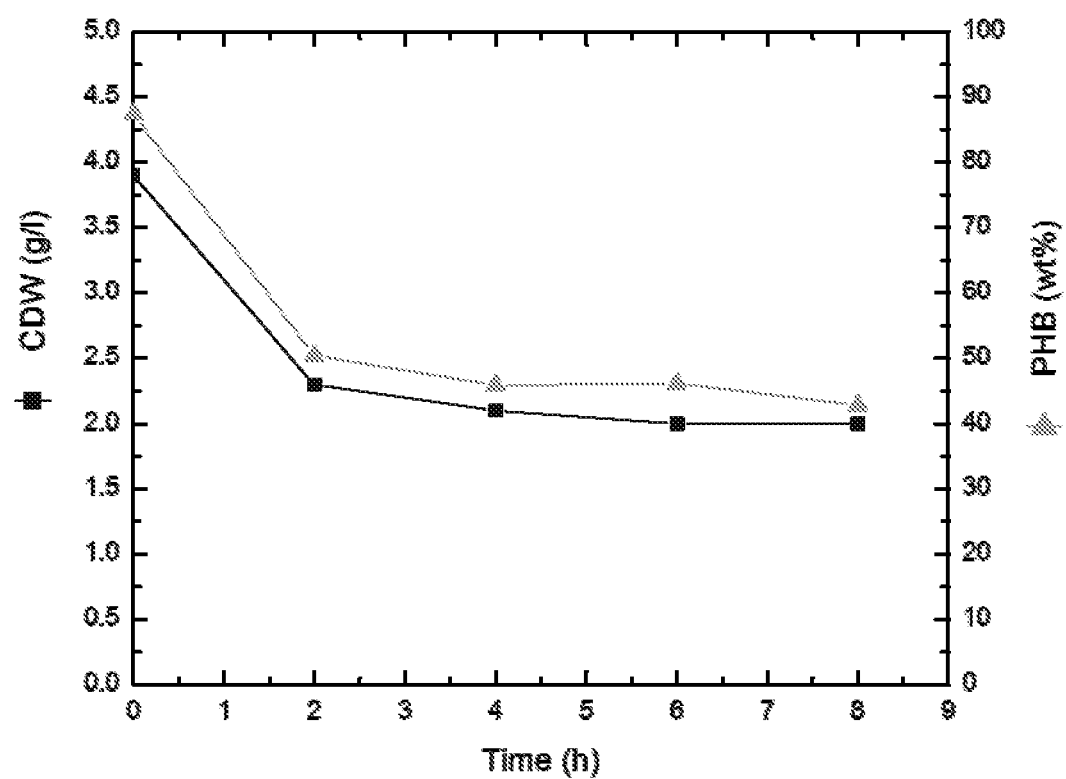

FIG. 9. shows a graph illustrating decrease in CDW of recovered pellets, and the decreased PHB content as percent of granules dry weight by the action of depolymerization, according to one aspect of the present invention i.e. cell-free enzyme depolymerization of PHA granules by thermostable PHA-depolymerase.

Figure 10:
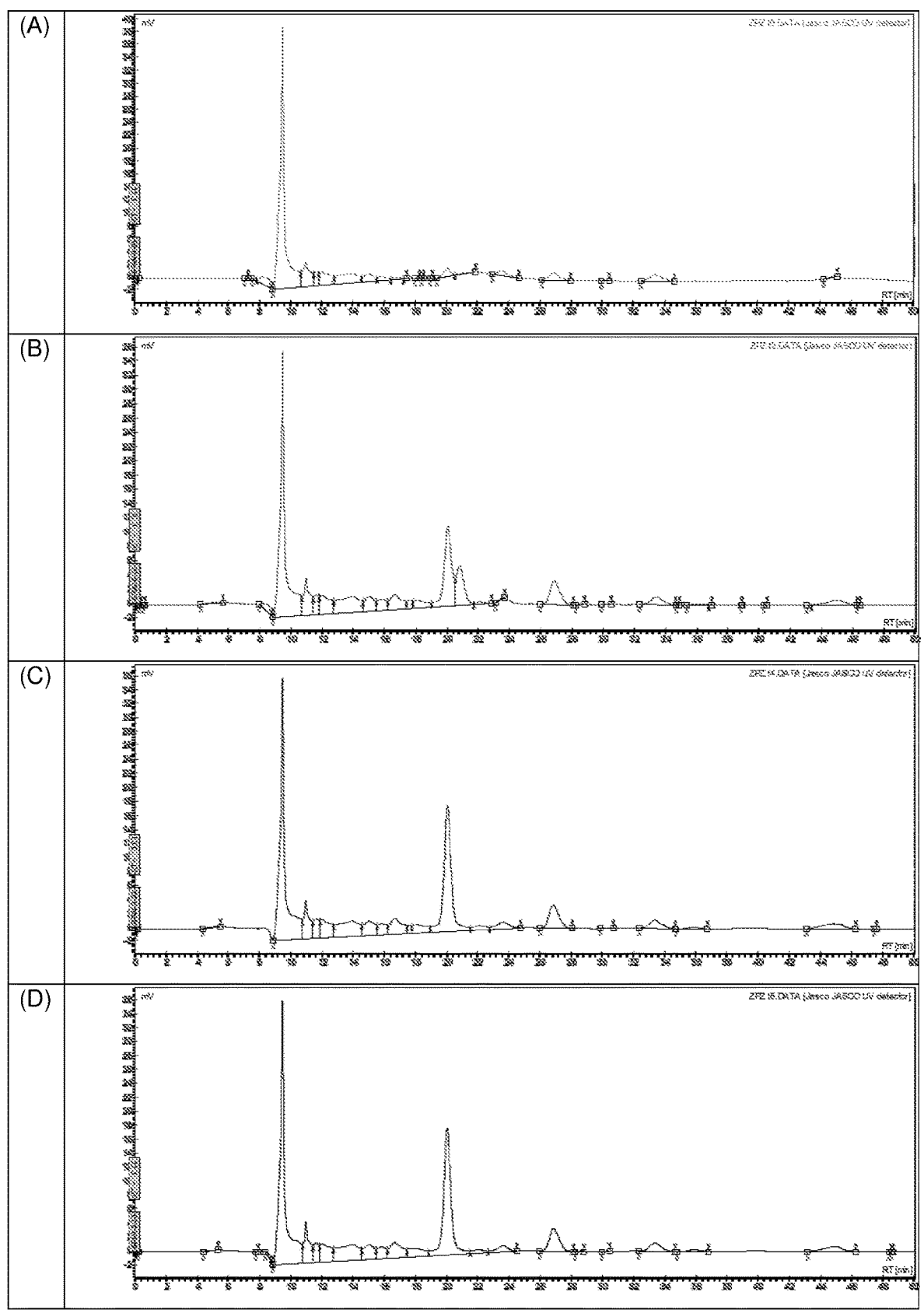

FIG. 10. shows chromatograms illustrating how a peak at about 20 minutes, symbolizing 3HB, which accumulated by time by the action of PHA-depolymerase enzyme and was not utilized as in case of PHA cell depolymerization.

DETAILED DESCRIPTION OF THE INVENTION

The present invention relates to a bio-based process for the extraction of bioplastics produced in microbial cells. The present invention further relates to a bio-based process for the production of monomers from said bioplastics. These processes are operated without the use of any chemicals, such as organic solvents, acid, alkali or other chemical additives. Thus, there is provided an organic solvent free and chemical free extraction and recovery of high-purity biopolymer granules from different bacterial strains. Also the bioplastics are obtained in a native form without any degradation or other losses. In addition to the bioplastics, non-bioplastic materials are also obtained during the extraction process. The non-bioplastic materials could comprise different cellular materials, such as lipids, nucleic acids, proteins, peptides and/or amino acids and other biochemical molecules. The present method of extraction involves the provision of microbial cells containing bioplastic materials. The bioplastics are accumulated as granules in the cytoplasm of the microbial cell. The cells containing the bioplastics are preferably bacterial or archaeal cells. To perform the extraction according to the present process, the mentioned cells containing the bioplastics are contacted with inoculum of bacterial cells of the genus *Bacillus*, preferably of the species *Bacillus pumilus*. The *Bacillus* cells act on the cell wall of the microbial cells containing the bioplastics, mainly they lyse it and utilize its constituents as nutrients for growth. In doing so, they disintegrate the cell structure of the bioplastic containing cells and uncover the bioplastic granules. The exposed bioplastic granules may then be collected.

The lysis of the bioplastic containing cells may be performed using one or several enzyme and/or other lysis affecting materials. The lysate obtained upon the lysis of the bioplastic containing cells is supposed to comprise exposed bioplastic (e.g. as granules), proteins, peptides, amino acids and other cell residues in aqueous solution. As disclosed above, the bioplastic may be removed and used as a high-end, high-purity product. It may also be used in further processes. Further, proteins, peptides and/or amino acids and other biomolecules may also be recovered as further value-added products.

Further, the process according to the present invention also enables production of the monomers of the recovered bioplastics by depolymerization. The depolymerization is achieved using depolymerising substances or microbial cells producing such depolymerising substances. Depolymerising substances may be chosen from enzymes and other depolymerization affecting substances. Depolymerization may be performed in one or more steps. As a one step process, depolymerising substances may be added to the bioplastics or the complete mixture from the extraction process containing the bioplastics. Alternatively, the bioplastics or the complete mixture from the extraction process containing the bioplastics disclosed above, may be contacted with microbial cells producing depolymerising substances. Then the bioplastics will be depolymerised upon contact with the produced depolymerising substances. The mixture formed may contain a mixture of monomers and oligomers. It is to be noted that the microbial cells producing the depolymerising substances may start acting on, e.g. consuming, the obtained monomers, which may result in a decreased yield of monomers. As long as cells producing depolymerising substances are present with monomers formed, there is a risk of the monomers being consumed by these cells. In order to overcome such an effect, the depolymerization may be performed in multiple steps. By providing a first step wherein a bioplastic or a mixture containing such a bioplastic is contacted with microbial cells producing depolymerising substances and allowed to react. When a desirable amount of depolymerising substances have been obtained from the cells, the reaction is terminated. The obtained mixture comprises cells, depolymerizing substances, polymers, monomers etc. A separation step separates depolymerizing substances from the other contents. The separated depolymerizing substances may then be used in a second step, and admixed with a bioplastic or a mixture containing such a bioplastic. This two-step process is a way to increase the yield of the monomers to be obtained.

The production of monomers from bioplastic produced according to the present process enables production of specific monomers in high purity. This method of producing monomers may be very attractive because of its simplicity, cost-efficiency, energy-efficiency, high product purity and low environmental impact. The monomers that may be obtained in enantiomerically pure form may be very difficult to obtain via conventional routes.

The present invention relates to a process for extraction of bioplastic from bioplastic-producing microbial cells, comprising the steps of:
  A. Providing producing microbial cells comprising bioplastic.
  B. Providing bacterial cells selected from the genus *Bacillus*
  C. Extracting the bioplastic by admixing the producing microbial cells of step A and the bacterial cells of step B and allowing lysis of bioplastic-producing microbial cells to take place.

This process renders it possible to extract bioplastic from producing microbial cells. The present invention provides an organic solvent free option, and therefore suggests a more cost-efficient and environment-friendly alternative technology to existing bioplastic extraction processes.

Another aspect of the present invention relates to a process of producing monomers from bioplastic, comprising the steps of:

D. Providing the bioplastic produced using the process for extraction of bioplastic from bioplastic-producing microbial cells mentioned above;

E. Providing microbial cells producing a depolymerization substance;

F. Depolymerising the bioplastic polymer by admixing the bioplastic of step D and the depolymerization substance-producing cells of step E and allow reaction, followed by removal of the depolymerization substance;

G. Providing bioplastic produced according to the process for extraction of bioplastic from bioplastic-producing microbial cells mentioned above;

H. Providing the depolymerization substance removed from step F;

I. Admixing bioplastic of step G and depolymerization substance of step H and allow reaction to obtain monomers of the bioplastic.

It should be noted that the process for extracting bioplastic from producing microbial cells and depolymerization of extracted polymer granules according to the present invention of course may comprise different standard components, such as various batch size, baffles, stirrers and so forth. Moreover, the design of the process for extracting bioplastic from producing microbial cells may vary, and the present invention, as formulated in the claims and exemplified within this application should be seen as embodying different forms of the product.

According to one aspect of the present invention, there is provided a process for extraction of bioplastic from bioplastic-producing microbial cells, comprising the steps of A. Providing bioplastic-producing microbial cells comprising bioplastic;

B. Providing bacterial cells selected from the genus *Bacillus*, such as *Bacillus pumilus*;

C. Extracting the bioplastic by admixing the bioplastic-producing microbial cells of step A and the bacterial cells of step B and allowing reaction.

A "bioplastic-producing microbial cells" as defined herein are cells of a microorganism capable of producing a bioplastic which may be extracted for further use.

"Bioplastics" as defined herein are plastics derived from renewable biomass sources, such as, but not limited to, sugars like glucose, sucrose, fructose, lactose, or xylose); vegetable fats and oils; methanol; glycerol; starch, cellulose, hemicellulose, lignin, or whey hydrolyzate; or gases (such as $CH_4$ or $CO_2$); or any combination or waste substrates or streams thereof. Petrochemical plastics, are derived from petroleum. Petrochemical plastics are based on fossil fuels and this contributes to the carbondioxide load. Some, but not all, bioplastics are biodegradable. Biodegradable bioplastics can be broken down in either anaerobic or aerobic environments, depending on their composition. There is a variety of materials that bioplastics can be composed of, such as, but not limited to, starches, cellulose, or other biopolymers; or any combination thereof.

In one embodiment the extraction of bioplastic from producing microbial cells is performed by cell lysis. In one specific embodiment, lytic bacterial cells from the species *Bacillus pumilus* are used, said cells, in contact with another bioplastic-producing microbial cells, contributes to an extraction reaction which may be lysis. As an example, the lytic bacterial cells contributing to the extraction may produce an extraction substance that break down the cell wall of the bioplastic-producing cell, liberating the bioplastic.

The bacterial cells used for extraction are in one embodiment part of the species *Bacillus pumilus* and the cellular features of *B. pumilus* are synonymous with other species of the genus *Bacillus* including *B. subtilis, B. megaterium, B. licheniformis*, and *B. cereus*. Therefore, extraction of bioplastics from bioplastic-producing microbial cells may be done with other bacterial cells than cells of the species *B. pumilus*. The present invention as described herewith is to be considered to embody various options of extraction species.

In one embodiment the lytic bacterial cells are selected from the group comprising 1T, 272T, 567T, ATCC 7061T, BCRC 11065T, BCRC 1706T, CCEB 639T, CCM 2144T, CCRC 11065T, CCRC 11706T, CCT 0513T, CCUG 26015T, CCUG 26016T, CECT 29T, CGMCC 1.3533T, CIP 52.67T, CN 2200T, CNCM 52.67T, DSM 27T, DSMZ 27T, Gordon 272T, GottheilT, HAMBI 1826T, IAM 12469T, IM 14177T, IAM 567T, IFO 12092T, JCM 2508T, KACC 10917T, KCTC 3348T, KCTC 3855T, LMD 48.24T, LMG 8928, LMG 7132T, LMG 7132 t1T, LMG 7132 t2T, Logan B0019T, LohnisT, Lohnis Kral GottheilT, Lohnis Kral Gottheil ATCC7061T, N. R. Smith 272T, N.R. Smith 272T, N.R.Smith272T, NBRC 12092T, NCCB 48024T, NCDO 766T, NCFB 1766T, NCIB 9369T, NCIM 9369T, NCIMB 9369T, NCTC 10337T, NRIC 1010T, NRRL NRS-272T, NRS-272T, OUT 8376T, PCM 1852T, Smith 272T, Smith N.R 272T, Smith N.R. 272T, Smith N.R., 272T, strain "Král"T, VKM 508T, VKM B-508T, VTT E-95572.T, GB34, SAFR-032, SAFR031, ATCC 7061, F036B, M11, M38, QST 2808, GHA 180, BU F-33 or FH9; or any combinations thereof.

In one embodiment the lytic bacterial cells are originated from the strain FH9 and in one specific embodiment said FH9 produces extracellular enzymes.

In another specific embodiment enzymes produced by the lytic bacterial cell may be proteases, glycosidases and/or lipases and in yet another specific embodiment the enzymes, such as proteases, glycosidases and/or lipases, act on the cell wall of the bioplastic-producing cells.

The present invention illustrates a process where various products may be collected and refined. In one embodiment the process further comprises a separation step, wherein proteins, peptides, amino acids, nucleic acids, and other biomolecules, or any combinations thereof are separated from the bioplastic.

The separation may be performed in various ways and some examples, however not exclusively, may be separation by decantation, filtration, centrifugation, aggregation, airflotation or precipitation or any combinations thereof. This step separate the plastic and renders it possible to further separate cellular components from the plastic. Examples of such components may, as previously mentioned, be proteins, peptides, amino acids, nucleic acids, and/or other biomolecules. Such cellular components may in further steps be collected and/or processed further.

The present invention is further compatible with various further process steps, when producing bioplastics, such as in one embodiment the process further comprises a washing step preferably after the extraction and separation, to wash the obtained removed bioplastic. This step cleans the plastic from remained cellular components. In one specific embodiment the washing step is performed using water as washing liquid.

It should be noted that the process for extracting bioplastics according to the present invention of course may comprise different steps, and also as having varied designs, which are not explicitly mentioned. Examples of such are one or more separation steps, concentration, stirring, controlling temperature and/or controlling pH, etc. Moreover, the design of the equipment used may vary, and the present invention, as according to the claims, should be seen as embodying different forms of equipments.

In one embodiment the extraction of bioplastic is accomplished with lytic bacterial cells from the species *B. pumilus*. In another embodiment the lytic bacterial cells are selected from the group biomass-degrading-enzymes producing microorganisms, such as protease/lipase/glycosidase-producing bacteria. In another specific embodiment the microbial cells containing bioplastics are selected from the group *Ralstonia eutropha, Halomonas boliviensis, Zobellella denitrificans* and recombinant *Eschericha coli*.

The lytic bacterial strain FH9 has been deposited, in accordance with the Budapest Treaty on the International Recognition of the Deposit of Microorganisms for the Purposes of Patent Procedure, at Leibniz-Institute DSMZ GmbH (Inhoffenstrasse 7 B, 38124 Braunschweig GERMANY) on 2014, Mar. 24 Number: DSM 28594.

In one embodiment of the present invention, the bioplastic is a polyester, preferably a linear polyester. In another, specific embodiment, the bioplastic could be, but not limited to, one of polyhydroxyalkanoates (PHAs), such as poly(3-hydroxypropionate) (PHP or P3HP), poly(3-hydroxybutyrate) (PHB or P3HB), poly(4-hydroxybutyrate) (P4HB), poly(3-hydroxyvalerate) (PHV or P3HV), poly(4-hydroxyvalerate) (P4HV), poly(5-hydroxyvalerate) (P5HV), poly(3-hydroxyhexanoate) (PHHx or P3HHx), poly(3-hydroxyoctanoate) (PHO, or P3HO), poly(3-hydroxydecanoate) (PHD or P3HD), poly(3-hydroxyundecanoate) (PHU, P3HU), or other short- or medium-chain length, saturated or unsaturated PHAs; or polylactic acid (PLA); or their copolymers or any combinations thereof.

As mentioned above, the present invention discloses an environment-friendly option to existing alternatives since in one embodiment, no organic solvent or chemicals or any combinations thereof are used in the process.

In one embodiment the bioplastic produced may be polylactic acid. The polymerisation of the lactic acid may occur in recombinant microbial cells by providing lactic acid-producing microbial cells with PHA synthase enzyme from said PHA synthesizing bacterial strain. Said polylactic acid may then be extracted as disclosed above, and optionally depolymerising the polymer to obtain enantiomeric monomers.

Herein purity of product is defined as percentage of bioplastic by weight in relation to the total amount of product. In one embodiment the present invention a biopolymer composition, obtainable by the process for extraction of bioplastic from bioplastic-producing microbial cells, is comprising a purity of biopolymer of at least 88%, preferably at least 90%, preferably at least 95%, preferably at least 97%, preferably at least 98%, and a recovery of at least 85% of the original PHA accumulated in the producing microbial cells.

In one specific embodiment, the invention comprises use of a bioplastic extracting process according to the present invention for the production of bioplastic with a purity of 95% and recovery of 85%, comprising no use of an organic solvent.

Bioplastics are used in various applications in the industry today, and are part of, or the sole component of, many consumer articles. Further, the bioplastic produced according to the present invention is biocompatible and implies use, for example, within the field of surgery.

In one embodiment, the invention comprises the use of a bioplastic extracted according to the process for extraction of bioplastic from bioplastic-producing microbial cells, for the production of products selected from the group comprising bioactive nanobeads (for example protein purification matrix), biocompatible products (for example implant parts, bone replacements), biodegradable products (for example slow release drug or fertilizer/pesticide carriers) or renewable thermoplast or elastomer products preferably chosen from the group comprising bags, boxes, bottles, cans, coatings, foils, diapers, wastebags, tyres, packaging, single use articles but not exclusively.

Almost all the non-PHA cellular materials of the PHA-accumulating cells were solubilised to a clear solution which could represent a proteins/amino acids rich preparation. This by-product could be of high interest as food additive or as complex nitrogen and vitamin supplement in microbial fermentation media as a cheap substitute for yeast extract. Animal, poultry, or fish feed application could be approved and accepted in respect to its non-animal origin.

In another embodiment, the invention comprises the use of a bioplastic extracting process, according to the present invention, for the production of proteins, peptides, amino acids and/or other biomolecules or any combinations thereof. In one aspect the invention relates to production of proteins, peptides and/or amino acids from proteinaceous biomass wastes. Said biomass wastes may be originated from the microbial fermentation industry or agro-, animal-, fish-, algae- or poultry industries.

Another aspect of the present invention relates to a process of producing monomers from bioplastic, comprising the steps of:

D. Providing the bioplastic produced using the process for extraction of bioplastic from producing microbial cells mentioned above;

E. Providing a depolymerization substance; and

F. Depolymerising the bioplastic polymer by admixing the bioplastic of step D and the depolymerization substance of step E and allow reaction.

According to one embodiment provision of a depolymerising substance of step E is performed by addition of microbial cells which produces said depolymerization substance.

In one embodiment the depolymerization substance may be an enzyme, e.g. a PHA extracellular depolymerase. The enzyme is used for the depolymerization of the bioplastic. In one embodiment the depolymerizing substance is provided via addition of microbial cells, producing said depolymerizing substance. In one embodiment the provision of enzyme is provided via addition of thermophilic PHA-degrading bacterial cells, which e.g. is producing thermostable extracellular PHA-depolymerase (s). In yet another embodiment the microbial cells used for depolymerization are *Schlegelella thermodepolymerans* or any other PHA-depolymerizing thermophilic or mesophilic microorganism (bacteria, actinomycetes or fungi). In one embodiment said depolymerizing substance is a PHA-extracellular depolymerase. In one specific embodiment said depolymerizing enzyme is a PHA-extracellular depolymerase and PHA oligomer hydrolase or any combinations thereof.

In yet another specific embodiment, the invention comprises the use of a bioplastic extracting process according to the present invention for the production of monomers, e.g. hydroxyalkanoate (HA) monomers.

In one embodiment the obtained monomers may be removed by a separation step.

If the depolymerising substance of step E is performed by addition of microbial cells which produce the depolymerization substance, then a separation step may be performed to remove the formed depolymerization substance from the depolymerization mixture.

If the depolymerization substance is removed, it may be used to further depolymerise bioplastic produced according to the process for extraction of bioplastic from bioplastic-producing microbial cells, according to the process below.

In another embodiment, if the depolymerization in step F is performed by addition of the depolymerization substance which was produced by microbial cells, said process further comprises the steps of:

G. Providing bioplastic produced according to the process for extraction of bioplastic from bioplastic-producing microbial cells mentioned above;
H. Providing the depolymerization substance from steps F to the bioplastic;
I. Admixing bioplastic of step G and depolymerization substance of step H and allow reaction, to obtain monomers of the bioplastic.

The depolymerization substance may be separated from the process mixture and reused further. When cells are used in step E and/or F, for production of the depolymerization substance for depolymerizing the bioplastic, i.e monomers are to be produced, steps G-I, preferably do not have cells present.

As indicated above there may be a reuse of said depolymerization substance. In one embodiment the invention comprises a separation step for provision of S. thermodepolymerans enzyme.

Another aspect of the present invention relates to a process of producing monomers from bioplastic, comprising the steps of:

D. Providing the bioplastic produced using the process for extraction of bioplastic from bioplastic-producing microbial cells mentioned above;
E. Providing microbial cells producing a depolymerization substance;
F. Depolymerising the bioplastic polymer by admixing the bioplastic of step D and the depolymerization substance-producing cells of step E and allow reaction, followed by removal of the depolymerization substance;
G. Providing bioplastic produced according to the process for extraction of bioplastic from bioplastic-producing microbial cells mentioned above;
H. Providing the depolymerization substance removed from step F;
I. Admixing bioplastic of step G and depolymerization substance of step H and allow reaction to obtain monomers of the bioplastic.

In one embodiment of the present invention the microbial cells producing the depolymerising substance are bacterial cells, preferably a thermophilic bacterial strain is used for the depolymerization of bioplastic. In another specific embodiment a thermostable PHA depolymerase is used for the depolymerization of bioplastic. Further, in one specific embodiment the PHA depolymerizing substance is an extracellular thermostable PHA depolymerase from *Schlegelella thermodepolymerans* or any other PHA depolymerizing microorganism (bacteria, actinomycetes or fungi).

One embodiment of the present invention illustrates a process of producing cellular proteinaceous byproducts, using the process according to the present invention including the step of separating the bioplastic extracted from the proteins, peptides and/or amino acids or any combination thereof. The proteins, peptides and/or amino acids may be considered as some of the thinkable products produced as a result of the present invention. Other products may be the monomers or the polymers produced as well as isolated extraction substances such as vitamins, enzymes, cofactors, lipids, carbohydrates, metabolites, osmolytes, and/or the like.

In another aspect the invention comprises the possible use of a bioplastic extracting and depolymerization processes for the production of other microbial intracellular polymers such as lipids (triacylglycerol, TAGs), polyanhydride particles (polyphosphate) or polysaccharides (glycogen), and the possible depolymerization into its constituents.

The process according to the present invention is a complete bio-based process for the extraction of bioplastics, PHAs, from the cells of the bioplastic-producing strains. It is assumed that this process can be applied for the extraction of PHAs from any accumulating strains or mixed cultures as it was proven using different PHA-producing strains in this invention. The purity of the granules could be easily improved by simple washing steps using only water or with commercial detergent. Autoclaving of the granules is an additional step to ensure the inactivation of any residual cells of the lysing bacteria.

The invention was extended to produce the monomer of, for example R-3HA as an easy and cost effective bio-based method for enantiomerically pure chemicals. R-3HA has numerous medical applications, such as its enhancing effect on cell proliferation. PHB was completely degraded by the thermophilic strain using its extracellular PHA depolymerase. The enzymatic bioconversion of the polymer into R-3HB was achieved at 70° C. using thermophilic PHA depolymerase crude preparation in a liter scale. This invention is a completely non-organic solvent, non-chemical extraction process for the bioplastics, PHAs, and for its monomers production, and this in addition to the amino acids rich by-product.

This technology might also be applied for the utilization of other microbial cellular materials remaining from any biotechnological process, where a huge cellular biomass could be converted into valuable product.

EXAMPLES

Process A: Extraction of PHA Granules from Producing Microbial Cells.

1) Cell Lysis Using a Lysing Microorganism as a Tool for PHA Granules Extraction from Different PHA-Producing Microbial Strains.

Harvested cells of PHA-producing strains after the desired accumulation period were used as wet cells (no need for usual drying step, a must for PHA extraction with solvents). The cell pellets of the PHA-producing strains were used as the main source of carbon and nitrogen. Pellets were sterilized in the optimum growth medium for the lysing microbial strain, basal medium, contains (g/l) $NH_4Cl$, 0.5; NaCl, 0.5; $K_2HPO_4$, 0.3; $KH_2PO_4$, 0.3; $MgCl$ $6H_2O$, 0.1; yeast extract, 0.1, casein, 5.0. Culture pH was adjusted at 7.5 prior to sterilization. Pre-cultures were prepared by full loop of well grown colony from plates into 250-ml Erlenmeyer flasks, both with the same medium. after inoculation, cultures were incubated at 37° C. for 24 h under shaking condition (180 rpm).

Cell lysis investigations were conducted in 1-l flasks containing 200 ml basal medium. Pre-culture of strain FH9 was used as lysis inoculum. In Lysis cultures, casein was repleased with two grams wet cell pellets of different PHA-accumulating strains, *Zobellella denitrificans* MW1, (3.04 g/l CDW, 65.4 wt % PHB); *Halomonas boliviensis* LC1 (4.43 g/l CDW, 70.2 wt % PHB); *Ralstonia eutropha* H16 (4.69 g/l CDW, 62.0 wt % PHB); recombinant *Eschericha coli* (1.39 g/l CDW, 0.0 wt % PHB), and lysis cultures were named ZdF, HbF, ReF, EcF, respectively. The pH of the culture was adjusted at 7.5 before sterilization. Flasks were incubated at temperature 37° C. and 180 rpm. Samples of 10-ml volume were taken for analyses at different incubation periods (0, 12, 26, 48, 72, and 240 h).

Culture broths were harvested after 10 days by centrifugation at 10000 rpm for 10 min. The recovered pellets were washed three times with distilled $H_2O$ and centrifuged at 6000 rpm for 10 min. Much slower speed could be applied to recover the aggregated granules, while most of the cells of the lysing strain, FH9, remain in the supernatant and can be separated easily by decantation.

Process A was conducted in a larger scale (3-l fermentor). Around 92 gram wet cells of *Z. denitrificans* (13.4 g/l CDW, 64.4 wt % PHB) were sterilized in 1500 ml basal medium. Well-grown pre-culture of strain FH9 (100 ml) was used as the lysis inoculum for the fermentor culture (ZdFF). Batch cultivation was performed in stirred tank fermentor at 37° C., pH 8.0, for 24 hours. Samples of 10-ml size were withdrawn from the fermentor at different time intervals for monitoring of the lysis reaction and for further biochemical analyses. After 24 hours, ZdFF culture was harvested by centrifugation at 10000 rpm for 20 min. Recovered lysis pellet was kept without washing at −20° C. for further analyses and application.

2) Washing of Extracted PHA Granules

Washing steps with water were included to recover PHAs of higher purity. Portions of two grams of wet lysis pellet from fermentor experiment, ZdFF, were mixed in 40 ml distilled water for 60 min at room temperature, with and without autoclaving. Addition of commercial detergent (100 µl) was also investigated. After washing, pure PHA granules were recovered by centrifugation of 10 ml portion of the mixture at 6000 rpm for 3 min, re-washed with distilled water or distilled water plus detergent, mixed at room temperature for 3 hours, then centrifuged at the same speed and time. Light microscopic examination was applied to follow the effect of washing on purification of the remaining cells and cell debris. Precipitation and decantation could also work, but the recovery and purity will differ then.

The pellets were then frozen and lyophilized for further GC and GPC analysis of PHA purity and molecular weight changes.

Process B: Depolymerization of PHA.

Depolymerization of Recovered PHA Granules was Performed to Produce the 3-Hydroxyalkanoic Acid Via a Completely Bio-Based Process.

A potent thermophilic strain for extracellular PHA-depolymerase production was used in this process. Part of the recovered unwashed PHA pellets recovered from process A (ZdFF) (18 g wet weight [4.4 g/l CDW] mainly contain extracted PHA granules plus some other lysis products and cells) were used as the sole carbon source for growth of the thermophilic strain. Pellets were sterilized in fermentor containing 1500 ml cultivation medium for the degrading thermophilic strain, mineral salts medium containing (g/l): $Na_2HPO_4.12H_2O$, 9.0; $KH_2PO_4$, 1.5; $MgSO.7H_2O$, 0.2; $NH_4Cl$, 1.0; $CaCl_2.2H_2O$, 0.02; $Fe(III)NH_4$-citrate, 0.0012; 1 ml of trace elements solution containing (g/l): EDTA, 50.0; $FeCl_3$, 8.3; $ZnCl_2$, 0.84; $CuCl_2$. $2H_2O$, 0.13; $CoCl_2.6H_2O$, 0.1; $MnCl_2.6H_2O$, 0.016; $H_3BO_3$, 0.1. Pellets from ZdFF was used as the sole carbon source.

Batch cultivation was performed in stirred tank fermentor at 50° C., pH 7.0, for 39 hours. Samples of 10-ml size were withdrawn from the fermentor at different time intervals for monitoring of depolymerization and for further biochemical analyses.

Process C: Enzymatic Depolymerization of PHA.

In a controlled fermentor experiment at 3-l scale, ten grams wet cell pellets from process A (ZdFF) were suspended in 1000 ml of the supernatant of process B. This supernatant works as cell-free crude preparation of the PHA depolymerizing enzyme. The depolymerization was performed at 70° C. and pH 8.2 for 8 hours. Products were monitored every two hours during the process via offline HPLC analysis.

Analyses:

Wet and dry weight. Cell wet weight (CWW), weight of the cell pellet after centrifugation at the assigned speed and time; cell dry weight (CDW), stable weight of the lyophilized cells.

GC analyses: 10-20 mg lyophilized cells or pellets were methanolyzed in chloroform and acidic methanol (15% $H_2SO_4$) for 3-4 hours at 100° C. Chloroform phase was used for GC analyses of 3-hydroxymethyl esters of PHA moieties. Lyophilized supernatants of process B and C were also methanolyzed and used to detect depolymerization products by GC.

Weight content of PHA (PHA wt %) was determined by GC in dry samples of known weight against standard sample of highly purified PHA, and used for purity and recovery calculation as well.

During processes B and C, HPLC was used for the detection of released microbial or enzymatic depolymerization products, 3-hydroxyalkanoic acid, from provided poly (3-hydroxyalkanoic acid) granules.

Light and transmission electron microscopic observations were done using fresh or frozen samples taken from cultures of the different processes, A, B, and C. Samples were prepared and investigated to study the physical effect of the lysing or depolymerizing microbial cells and/or enzyme on PHA-accumulating microbial cells or on the recovered PHA granules, and the appearance or predominance of different growing, lysing, lysed, or depolymerizing cells during the studied processes.

Gel permeation chromatography (GPC) was used to determine the effect of the bio-extraction process on the molecular weight of the recovered polymer, process A.

Results

1. Process A: Lysis of PHA-Producing Microbial Strains.

1.1. Lysis of Different PHA-Producing Microbial Strains. Many bacterial strains are used for the production of PHA in laboratory and industrial scale. Practically, for each process and/or strains, a defined extraction method is assigned. None can work perfectly with all strains and all PHA kinds. In the present technology, a new bio-based extraction method using the bacterial strain, *Bacillus pumilus* FH9, was operated for the extraction of PHA granules from different PHA-bacterial producers. Cells of strain FH9 were induced to hydrolyze the non-PHA cellular materials of different PHA accumulating strains as being the sole source of nutrients in the lysis medium and that leads to the induction of cell wall hydrolysing enzymes by the strain FH9.

Strains *Ralstonia eutropha* H16, recombinant *Eschericha coli*, *Zobellella denitrificans* MW1, *Halomonas boliviensis* LC1, are some of the well studied bacteria, those known to produce PHA from different carbon sources like glycerol, glucose, sucrose, starch, or other cheap substrates. Cells of these strains were cultivated separately at the standard conditions for PHA accumulation (PHA content 60-70 wt %), then harvested and transferred to the lysis medium (growth medium for strain FH9). Recombinant *E. coli* cells with no PHA content was used as negative control for the experiment.

Upon inoculation with the lytic strain, FH9, lysis reaction was monitored by the decrease in cell dry weight of harvested pellets (FIG. 2 A), and the increase in its PHB content (FIG. 2 B). A clear decrease in CDW was recorded for all PHA accumulating strains as shown in FIG. 2 A. After 48 h almost all non-PHA cellular materials was solubilized as revealed by the increase in PHB content till the maximum values, 93.6, 96.0, and 91.6 wt %, for cells of strains, *Z. denitrificans, H. boliviensis*, and *R. eutropha*, respectively. Longer incubation time affect the purity of the recovered PHA granules, may be by the increased cell mass of the growing lytic cells. Most of the lysis effect was achieved within the first 26 h. In this context, it is very important to optimize the extraction time to reach proper lysis while keeping low cell density of the lytic cells, for easy separation of high pure PHA granules. Even though strain FH9 shows lysis activity on all studied PHA-accumulating strains, the purity of recovered PHA granule from strains *Z. denitrificans* and *H. boliviensis* was more than that from *R. eutropha*. This may be because of the difference in cellular structure of the cells being lyzed or because of the difference in cellular growth mass of the lytic cells on each strain which may be difficult to separate from the released PHA granules.

1.2. Large-Scale Lysing of PHA-Accumulating Cells for PHA Extraction.

A study at 3-liter bioreactor scale was conducted for the recovery of PHA granules from strain *Z. denitrificans* (64.4 wt %, PHB). PHA-containing cells as wet pellets were sterilized in basal medium and used as the sole source for both carbon and nitrogen. A small amount of yeast extract (0.1 g/l) was added as a growth initiator. The culture was inoculated with active inoculum of strain FH9 which showed fast growth and utilization of *Z. denitrificans* non-PHA cellular materials, as detected by the increase of PHB content in the harvested pellets from 64.4 to 83.8 wt % (FIG. 4).

Electron microscope images (FIG. 3) show dramatic physical disruption of cell wall and other non-PHA cellular materials, even after only 6 hours of the inoculation with strain FH9 (FIG. 3B). With increase in fermentation time, PHA granules were released completely and appear to be free of other cellular materials. Some free granules were seen to merge together (FIG. 3B, C; size 0.3-1.0 μm) forming granules larger than the size of normal granules inside the cells (FIG. 3 A; size <0.3 μm). It was also noticed that the predominance of FH9 cells (rod cells) increased with time between 6 h and 24 h (FIG. 3 B, C).

The microscopic graph in FIG. 3 C shows the complete spherical shape of the recovered PHA granules in a mixture with cells of strain FH9. Some granules are seen to have other cellular material around. This may be the reason of low purity of the recovered PHA detected by GC (not washed pellets from process A) (FIG. 4). However it is clear that during the first 12 hours, significant improved purity has been achieved as a result of the hydrolysis of non-PHA cellular materials by the action of the lytic strain, *B. pumilus* FH9.

Lysis time of 12 hours seems enough for release of PHA granules after lysing the other cellular materials. PHB content in this recovered mixture increased from 64.4 wt % to 81.8 wt %. Slightly higher PHB content was reached by the increased lysis time, maximum PHB content was achieved at 20 h (83.8 wt %). Very high PHB recovery was achieved when 97-100% of the cellular content of PHA before the lysis was recovered at the end of the culture. Separation and washing of the released granules from the culture broth could give higher purity polymer granules. This relatively short time is very promising for industrial application of the process. As a single-step extraction if compared with other reported shorter but multiple-step extraction processes.

1.3. Recovery of Pure PHA Granules.

The product of the lysis process using strain FH9 was a mixture of PHA granules with some non-PHA molecules, probably attached proteins and/or lipids in addition to the growing FH9 cells. This mixture was easily recovered by centrifugation. Additional separation step is needed to separate the PHA granules from some of the growing lysing cells and lysis products.

A simple washing step was studied for the recovery of PHA granules. This was combined with the effect of autoclaving for sterilization that would kill the lysing cells and/or enzymes. Commercial detergent was employed to get rid of cells or proteinaceous materials which may be attached to PHA granules. After mixing for 3 hours at room temperature, both pellet and supernatant were checked under light microscope. In the supernatant, some intact cells of strain *Z. denitrificans* were still suspended in the supernatant after a low speed centrifugation, while the aggregated granules were precipitated easily.

Washing of recovered pellets with water significantly improved the purity of recovered PHB from 82.2 wt % to 91.5 wt %. Further improved purity (up to 94.5 wt %) was achieved when detergent was used during washing. Washing could not improve the purity if the pellets were autoclaved before washing. It could be revealed that the harsh condition during autoclaving made it very difficult to separate PHA granules from other contaminants proteins, cells, or cell debris. If autoclaving is a necessity, better to autoclave the purified granules after washing and not before (Table 2). At the maximum PHB purity achieved (94.5 wt % PHB), high polymer recovery was maintained (84.5 wt %). This recovery achieved is ideally the same as the maximum recovery reported for chloroform extraction, however, the purity was slightly higher (98.3 wt %) (Table 2).

The effect of long lysis time on the molecular weight (MW) of recovered PHB was analyzed by GPC at the end of the ten-day lysis culture. PHB with MW of 478618, 1009779, and 887406 Da, were recovered from strains *Z. denitrificans, H. boliviensis, R. eutropha*, respectively (Table 1). This proves that no destructive effect on MW was recorded for recovered PHB from all studied strains, in comparison with the solvent extracted PHB from cells of the same strains (Table 1), or the previously reported MW of PHB from *H. boliviensis, R. eutropha*. This long lysis time was applied to study if there will be a negative effect of lysing cells on the recovered polymer. This ensures the inability of strain FH9 to degrade the targeted polymer while degrading the non-PHA cellular materials.

Moreover, the molecular weight of recovered PHB from *Z. denitrificans* was not affected by the applied washing step with water and/or detergent as almost the same MW values was recovered after washing (Table 2).

TABLE 1

GPC analysis of lysis-recovered PHB from different accumulating strains.

| Sample | Molecular weight (Da) | PHB content (wt %) |
|---|---|---|
| Pure PHB from Zd (CHCl$_3$ extraction) | 497956 | 100.0 |
| Pure PHB from Hb (CHCl$_3$ extraction) | 1012314 | 100.0 |
| ZdF* | 478618 | 84.6 |
| HbF | 1009779 | 89.6 |
| ReF | 887406 | 87.5 |

*ZdF, HbF, ReF are washed pellets from lysis experment in flasks.

TABLE 2

Effect of washing on purity and molecular weight of recovered PHB

| Sample | Molecular weight (Da) | PHB content (wt %) | PHB recovery (wt %) |
|---|---|---|---|
| Pure PHB from Zd (CHCl$_3$ extraction) | 497956 | 98.3** | 85.0** |
| ZdFF* non-autoclaved + H$_2$O + det.*** | 498562 | 94.5 | 84.5 |
| ZdFF Autoclaved + H$_2$O + det.*** | 549971 | 86.8 | 100.0 |
| ZdFF non-autoclaved + H$_2$O | 519824 | 91.5 | 93.9 |
| ZdFF Autoclaved + H$_2$O | 482440 | 86.1 | 100.0 |

*ZdFF is washed pellet from lysis experment in fermentor.
**Reported data.
***Commercial detergent.

2. Process B: Bacterial Depolymerization of PHA.

Production of enantiomerically pure 3-hydroxyalkanoic acids has got much interest during the last years due to its importance as precursors for tailor-made polymers, and also for many medicinal and biotechnological applications. In this respect, a second process was designed for the conversion of recovered PHA granules from process A to its monomers via cell/enzyme depolymerization. The assigned PHA-depolymerizing strain is a thermophilic bacterium with optimal growth and PHA depolymerization ability at 50° C. As shown in FIG. 6, within only 6 hours, PHA content of the pellets decreased from 87.4 wt % to 56.4 wt %; PHA granules were completely depolymerized within 39 h, as shown in the electron microscpic graphs in FIG. 5. It was also clear that the depolymerzing cells while being able to degrade all released PHA granules, could not attack PHA granules which still existed inside some intact Z. denitrificans cells not lyzed by strain FH9 during process A (FIG. 5 B).

Scanning electron microscopic graph (FIG. 5 C) also shows a direct contact of the PHA-depolymerizing cells on the degradation of PHA granules during growth. The granules are used as the sole source of carbon for the depolymerizing cells.

A clear peak of released monomer, 3HB, was detected by HPLC at retention time 20 min (FIG. 7 B). It was also recorded that, by the increase in cultivation time, this peak disappeared. This should be because of the utilization of depolymerization products by the growing cells. In this context, a shorter incubation time is recommended to induce PHA-depolymerizing cells only to produce extracellular PHA depolymerases which can be used for cell-free enzyme depolymerization of PHA granules. This strategy will prevent further utilization of the degradation products as happened in the case of growing depolymerizing cells.

3. Process C: Enzymatic Depolymerization of PHA for 3-HA Production.

The depolymerization of recovered PHA granules from process A to produce 3-HA was investigated in cell-free enzyme depolymerization process. This process was operated to prevent the utilization of produced monomers by the depolymerizing cells. The supernatant of process B at 39 h was used as a crude PHA-depolymerase enzyme. Even though this crude enzyme was harvested at the end of PHA-cell depolymerization culture, it showed a noticeable depolymerization within only two hours at 70° C., the optimum temperature for enzyme activity, and PHA content decreased to 50.4 wt % (FIG. 9). Over 50% of PHA content was depolymerized within 8 hours, and a degradation product was detected by HPLC analysis at retention time of 20 min (FIG. 10), the same peak that was recorded in process B. For confirmation, both supernatents of process B (39 h) and process C (8 h) were lyophilized and subjected to methanolysis for GC analysis of depolymerization products. 3-hydroxymethyester was detected in process C supernatant, but was not detected in process B. GC analysis revealed that 24.8 wt % of the lyphilized supernanent from process C is 3-hydroxymethyester.

Interestingly, in electron microscope graph (FIG. 8), the spherical shape of PHA granules is clearly attacked from one side (FIG. 8 A, B) by the action of the depolymerase enzyme as a direct physical contact to facilitate the depolymerization process.

In FIG. 8 B, some rod cells can still be seen in this enzymatic process. These cells could be either cells of strain FH9 remaining in the pellets from process A, or cells of strain S. thermodepolymerans present in the supernatant of process B, i.e. in the crude enzyme preparation itself.

The invention claimed is:

1. A process for extraction of bioplastic from bioplastic-producing microbial cells, comprising the steps of:
   A. providing a composition of bioplastic producing microbial cells having cell walls, the cells containing bioplastic as granules;
   B. providing active bacterial cells selected from the species *Bacillus pumilus* having the ability to lyse the cell walls of the bioplastic-producing microbial cells;
   C. lysing the bioplastic producing microbial cells by contacting the bioplastic-producing microbial cells of step A and the bacterial cells of step B and allowing reaction, where said contacting active *B. pumilus* cells does not consume bioplastic from the bioplastic-producing microbial cells; and
   D. applying a procedure of recovery of the bioplastic from the lysing of the microbial cells of step C, which procedure of recovery can be repeated after washing the bioplastic, wherein recovery is of an amount of at least 85% of the bioplastic of step A, a purity of at least 88% by weight, and a molecular weight distribution consistent with the bioplastic of step A;
   wherein said lysing and recovering steps are organic solvent free and chemical free.

2. The process according to claim 1, wherein the lysis step comprises lysis by the active bacterial cells or by extracellular enzymes of the active bacterial cells.

3. The process according to claim 1, wherein the extraction process further is comprising a separation step, wherein proteins, peptides, or amino acids or any combinations thereof are separated from the bioplastic granules.

4. The process according to claim 3, wherein the separation is performed by decantation, filtration, centrifugation, aggregation, air flotation or precipitation or any combinations thereof.

5. The process according to claim 3, further comprising a washing step after extraction and separation to wash the obtained bioplastic granules.

6. The process according to claim 1, wherein the bioplastic-producing microbial cells are selected from the group *Ralstonia, Halomonas, Zobellella, Pseudomonas, Alcaligenes, Bacillus, Chromobacterium*, recombinant *Eschericha coli*, or any combinations thereof or other bioplastic-producing microbial cells, or mixed cultures.

7. The process according to claim 1, wherein the bioplastic is a polyester.

8. The process according to claim 1, wherein the bioplastic is selected from polyhydroxyalkanoates (PHAs): poly(3-hydroxypropionate) (PHP or P3HP), poly(3-hydroxybutyrate) (PHB or P3HB), poly(4-hydroxybutyrate) (P4HB), poly(3-hydroxyvalerate) (PHV or P3HV), poly(4-hydroxyvalerate) (P4HV), poly(5-hydroxyvalerate) (P5HV), poly(3-hydroxyhexanoate) (PHHx or P3HHx), poly(3-hydroxyoctanoate) (PHO, or P3HO), poly(3-hydroxydecanoate) (PHD or P3HD), poly(3-hydroxyundecanoate) (PHU, P3HU), or other short- or medium-chain length, saturated or unsaturated PHAs; or polylactic acid (PLA); or their copolymers or any combinations thereof.

9. The process according to claim 1, wherein the bioplastics are obtained in a native form without any degradation.

10. The process according to claim 2, wherein said lysing bacterial cell is originated from strain FH9.

11. The process according to claim 5, wherein said washing step is performed using water as washing liquid.

12. The process according to claim 7, wherein the bioplastic is a linear polyester.

13. The process according to claim 1, wherein the bioplastic is polyhydroxyalkanoate (PHA).

14. The process according to claim 1, wherein the bioplastic has a purity of biopolymer of at least 95%.

15. The process according to claim 1, wherein the bioplastic has a purity of biopolymer of at least 90%.

\* \* \* \* \*